(12) United States Patent
Frankle

(10) Patent No.: US 6,790,234 B1
(45) Date of Patent: Sep. 14, 2004

(54) REVERSE SHOULDER PROSTHESIS SYSTEM

(76) Inventor: Mark A. Frankle, 5124 Longfellow Ave., Tampa, FL (US) 33629

( * ) Notice: Subject to any disclaimer, the term of this patent is extended or adjusted under 35 U.S.C. 154(b) by 294 days.

(21) Appl. No.: 10/038,210

(22) Filed: Jan. 4, 2002

(51) Int. Cl.$^7$ .................................................. A61F 2/40
(52) U.S. Cl. .................................................. 623/19.12
(58) Field of Search .......................... 623/19.11, 19.12, 623/19.13, 19.14

(56) References Cited

U.S. PATENT DOCUMENTS

| | | | | |
|---|---|---|---|---|
| 3,916,451 A | * | 11/1975 | Buechel et al. ............ | 623/23.4 |
| 3,978,528 A | * | 9/1976 | Crep ........................ | 623/19.12 |
| 4,693,723 A | * | 9/1987 | Gabard ..................... | 623/19.12 |
| 5,723,018 A | * | 3/1998 | Cyprien et al. .......... | 623/19.13 |

* cited by examiner

Primary Examiner—David J. Isabella
Assistant Examiner—Kamrin Landrem
(74) Attorney, Agent, or Firm—Edward P. Dutkiewicz

(57) ABSTRACT

A reverse shoulder prosthesis system has a humeral stem with a lower cylindrical portion, an upper cylindrical portion, an intermediate conical portion, and a central axis, a large flat with a small recess having an axis forming an angle of about 150 degrees to the central axis. A humeral socket has an upper surface machined as a hemisphere and an attached backing plate formed with a projection as a male Morse taper received in the small recess of the stem. A glenoid head is formed in a hemispherical configuration with a cylindrical pocket. A baseplate has a cylindrical central part, an exterior part, a long cancellous bone screw machined in the center of the exterior part, and an enlarged interior projection for assembly to the head.

7 Claims, 3 Drawing Sheets

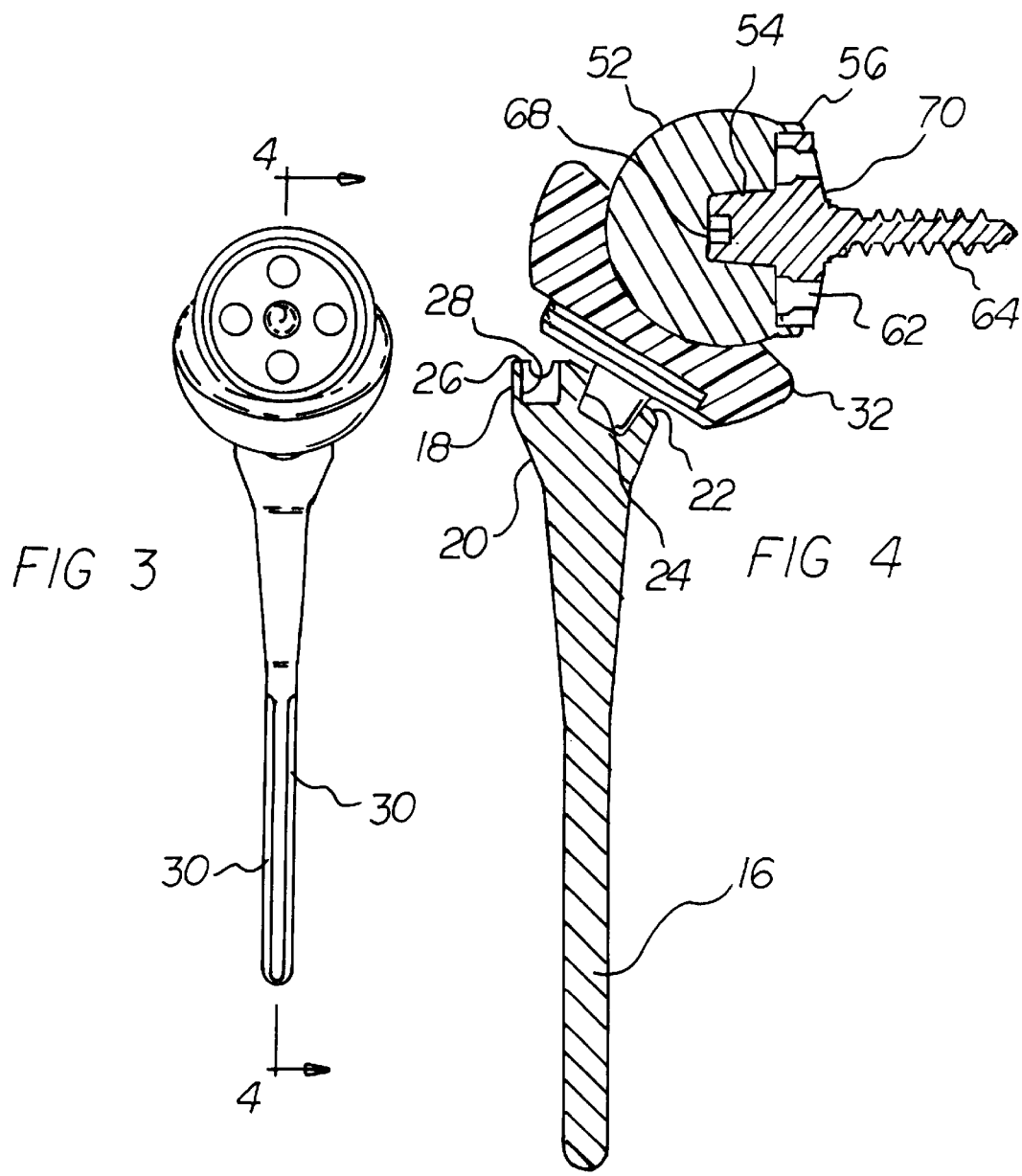

REVERSE SHOULDER PROSTHESIS SYSTEM

BACKGROUND OF THE INVENTION

1. Field of the Invention

The present invention relates to a reverse shoulder prosthesis system and more particularly pertains to providing a shoulder prosthesis with improved fabrication, installation and utilization capabilities.

2. Description of the Prior Art

The use of shoulder prosthesis systems of known designs and configurations is known in the prior art. More specifically, shoulder prosthesis systems of known designs and configurations previously devised and utilized for the purpose of facilitating the fabrication and/or installation and/or utilization of shoulder prosthesis systems through known methods and apparatuses are known to consist basically of familiar, expected, and obvious structural configurations, notwithstanding the myriad of designs encompassed by the crowded prior art which has been developed for the fulfillment of countless objectives and requirements.

By way of example, U.S. Pat. Nos. Des. 243,884 and Des. 283,885 both to Fenlin disclose a shoulder prosthesis. U.S. Pat. No. 3,978,528 to Crep discloses a bone and joint prosthesis. U.S. Pat. No. 4,106,128 to Greenwald discloses a endoprosthetic bone joint. U.S. Pat. No. 4,693,723 to Gabard discloses shoulder prosthesis. U.S. Pat. No. 4,908,036 to Link discloses an endoprosthesis. U.S. Pat. No. 5,462,563 to Shearer discloses an orthopaedic implant. U.S. Pat. No. 5,702,457 to Walch discloses a humeral prosthesis incorporating a sphere. See also *Delta Shoulder Prosthesis for Rotator Cuff Rupture* by P. M. Grammont and E. Baulot from *Delta Shoulder Prosthesis* dated January 1993, pages 65–68.

While these devices fulfill their respective, particular objectives and requirements, the aforementioned patents do not describe a reverse shoulder prosthesis system that allows providing a shoulder prosthesis with improved fabrication, installation and utilization capabilities.

In this respect, the reverse shoulder prosthesis system according to.the present invention substantially departs from the conventional concepts and designs of the prior art, and in doing so provides an apparatus primarily developed for the purpose of providing a shoulder prosthesis with improved fabrication, installation and utilization capabilities.

Therefore, it can be appreciated that there exists a continuing need for a new and improved reverse shoulder prosthesis system which can be used for providing a shoulder prosthesis with improved fabrication, installation.and utilization capabilities. In this regard, the present invention substantially fulfills this need.

SUMMARY OF THE INVENTION

In view of the foregoing disadvantages inherent in the known types of shoulder prosthesis systems of known designs and configurations now present in the prior art, the present invention provides an improved reverse shoulder prosthesis system. As such, the general purpose of the present invention, which will be described subsequently in greater detail, is to provide a new and improved reverse shoulder prosthesis system and method which has all the advantages of the prior art and none of the disadvantages.

To attain this, the present invention essentially comprises a humeral stem fabricated of titanium. The stem is designed to allow efficient machining of the stem from titanium bar stock in lieu of expensive tooling for forgings. The humeral stem has a lower cylindrical portion having a diameter of between about 6 millimeters and 10 millimeters. The humeral stem also has an upper cylindrical portion having a diameter of between about 8 millimeters and 14 millimeters. An intermediate conical portion is provided between the lower and upper cylindrical portions. The lower, upper and intermediate portions have a common central axis. The stem has a large flat machined on the posterior proximal portion of the stem. The large flat has a small recess formed as a female Morse taper for assembly of a humeral socket. The stem also has a small flat machined on the anterior proximal portion of the stem. The small flat has a threaded insertion/extraction hole. These allow ease of fixturing for machining and give rotational stability when implanted. The small recess has an axis forming an angle of about 150 degrees to the central axis. The prior art primary stems are at 135 degrees. The added 15 degrees allows the stem to be more medial which allows for proper tension relationship with the deltoid and increases the range of motion. The lower portion of the stem has four axial cement grooves distally for added fixation and rotational stability. The stem is designed to be seated approximately 12 millimeters below the humeral osteotomy. The proximal humeral bone is reamed so the humeral socket.can be recessed to thereby provide for proper tension and bone support of the structural socket and the deltoid and increased range of motion. Next provided is a humeral socket. The socket is fabricated of ultra high molecular weight polyethylene. A backing plate fabricated of titanium is attached to the socket. The backing plate has an upper generally cylindrical extent. The backing plate also has a lower extent formed with a projection as a male Morse taper. The projection is adapted to be received in the small recess of the stem. The socket has an upper surface machined as a 32 millimeter diameter hemisphere for the receipt of a glenoid head. This allows for 4 millimeters of wear by the polyethylene socket. The polyethylene captures about one-third of the glenoid head. The backing plate is formed with a linear recess machined adjacent to the bottom of the socket after assembly. A locking pin extends through a recess in the socket to prevent the backing plate from backing out of the socket. A 2 millimeter lip is formed around the bottom of the backing plate adjacent to the linear recess to provide lever-out stability with the socket. The sizes are neutral, about +4 millimeters and +8 millimeters. A glenoid head fabricated of cobalt chrome is next provided. The glenoid head is formed in a hemispherical configuration with a 32 millimeter diameter. The glenoid head is adapted to be received in the socket. A machined cylindrical pocket and a glenoid baseplate are provided. The pocket allows the head to mate with the glenoid baseplate with no gap. The head has a large recess formed as a female Morse taper for assembly to a glenoid baseplate. The head has a small cylindrical neck adjacent to the pocket to prevent contact of the socket in articulation. There is one head height. Lastly, a baseplate is fabricated of titanium. The baseplate is machined from titanium bar. The baseplate has a cylindrical central part having a diameter of 26 millimeters. Four mounting screw holes are equally spaced and extend through the cylindrical central part and four 3.5 millimeter screws are provided for fixation. The holes and screws are off-axis to allow 12 degrees angulation of screws in any direction. A 6.5 millimeter by 2.5 millimeter long cancellous bone screw is machined in the center of the exterior part of the baseplate which provides greater fixation. An enlarged interior projection has a male Morse taper for assembly to the head. A 3.5 millimeter hexagonal recess is formed in the end of the interior projection to assist during insertion. The baseplate also includes a titanium porous coating for bone in-growth.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved reverse shoulder prosthesis system which has all of the advantages of the prior art shoulder prosthesis systems of known designs and configurations and none of the disadvantages.

It is another object of the present invention to provide a new and improved reverse shoulder prosthesis system which may be easily and efficiently manufactured and marketed.

It is further object of the present invention to provide a new and improved reverse shoulder prosthesis system which is of durable and reliable constructions.

An even further object of the present invention is to provide a new and improved reverse shoulder prosthesis system which is susceptible of a low cost of manufacture with regard to both materials and labor, and which accordingly is then susceptible of low prices of sale to the consuming public, thereby making such reverse shoulder prosthesis system economically available to the buying public.

Even still another object of the present invention is to provide a reverse shoulder prosthesis system for providing a shoulder prosthesis with improved fabrication, installation and utilization capabilities.

Lastly, it is an object of the present invention to provide a new and improved reverse shoulder prosthesis system having a humeral stem with a lower cylindrical portion, an upper cylindrical portion, an intermediate conical portion, and a central axis, and a large flat with a small recess having an axis forming an angle of about 150 degrees to the central axis. A humeral socket has an upper surface machined as a hemisphere and an attached backing plate formed with a projection as a male Morse taper received in the small recess of the stem. A glenoid head is formed in a hemispherical configuration with a cylindrical pocket. A baseplate has a cylindrical central part, an exterior part, a long cancellous bone screw machined in the center of the exterior part, and an enlarged interior projection for assembly to the head.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a front elevational view taken along line 3–3 of FIG. 2.

FIG. 4 is a cross sectional view taken along line 4–4 of FIG. 3.

The same reference numerals refer to the same parts throughout the various Figures.

DESCRIPTION OF THE PREFERRED EMBODIMENT

Figures 1, 2:
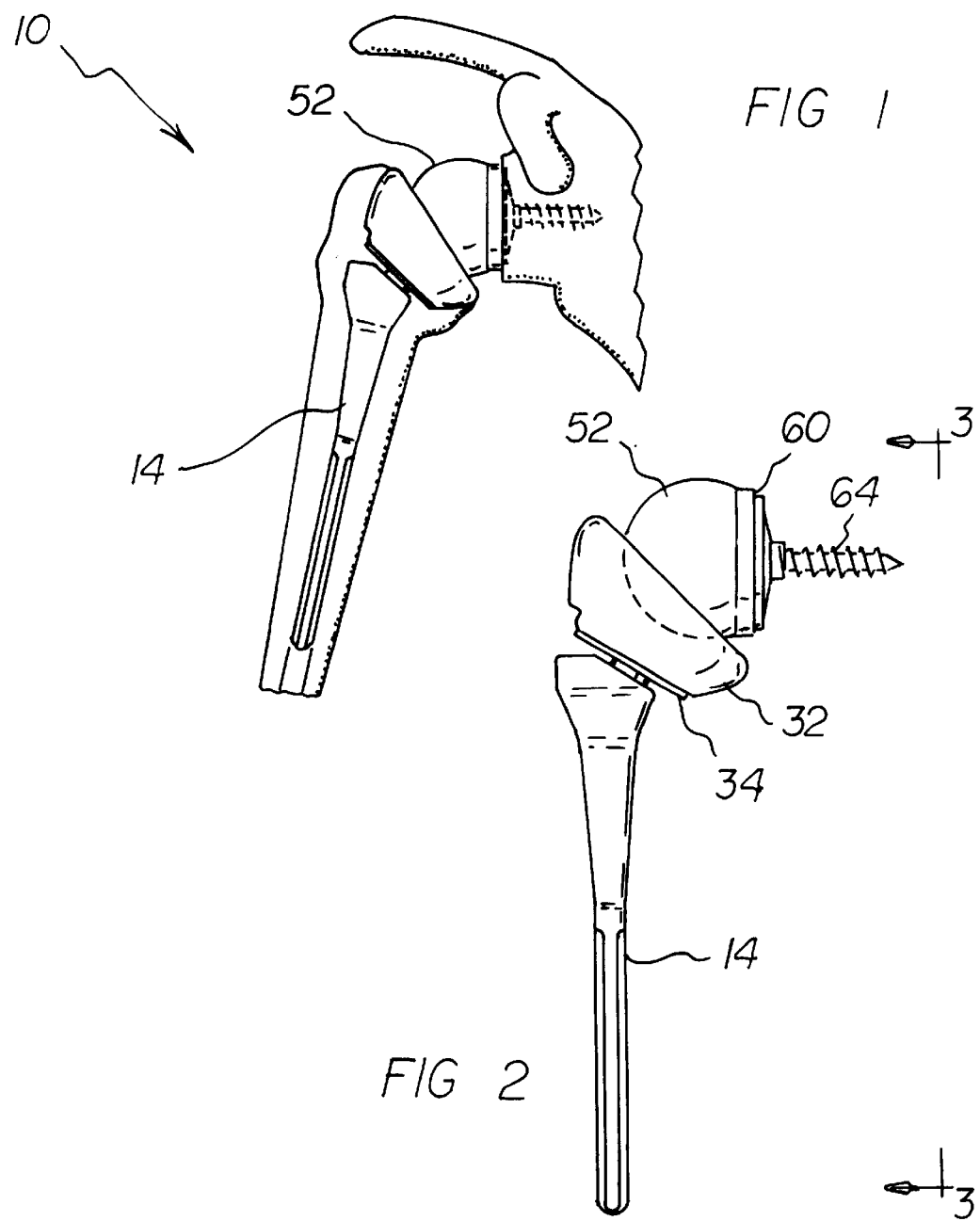
FIG. 1 is a front elevational view of the new and improved reverse shoulder prosthesis system constructed in accordance with principals of the present invention.
FIG. 2 is a front ,elevational view similar to FIG. 1 but enlarged while eliminating the humerus and clavicle.
Figure 5:
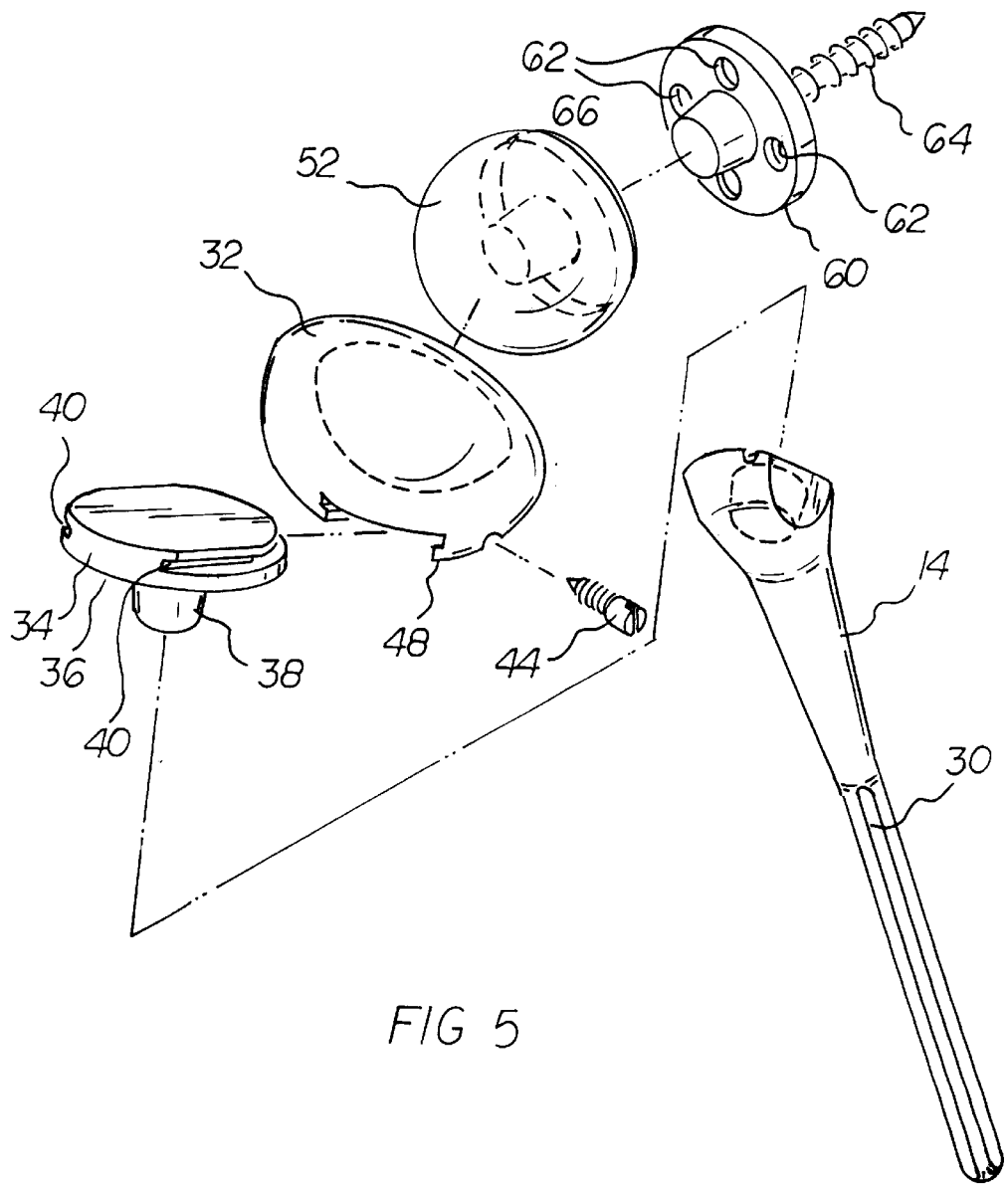
FIG. 5 is an exploded perspective view of the system showing the prior Figures.

With reference now to the drawings, and in particular to FIG. 1 thereof, the preferred embodiment of the new and improved reverse shoulder prosthesis system embodying the principles and concepts of the present invention and generally designated by the reference numeral 10 will be described.

The present invention, the reverse shoulder prosthesis system 10 is comprised of a plurality of components. Such components in their broadest context include a humeral stem, a humeral socket, a glenoid head, and a baseplate. Such components are individually configured and correlated with respect to each other so as to attain the desired objective.

First provided is a humeral stem 14. The humeral stem is fabricated of titanium. The stem is designed to allow efficient machining of the stem from titanium bar stock in lieu of expensive tooling for forgings. The humeral stem has a lower cylindrical portion 16 having a diameter of between about 6 millimeters and 10 millimeters. The humeral stem also has an upper cylindrical portion 18 having a diameter of between about 8 millimeters and 14 millimeters. An intermediate conical portion 20 is provided between the lower and upper cylindrical portions. Various sizes may be employed as a function of the particular application. The lower, upper and intermediate portions have a common central axis. The stem has a large flat 22 machined on the posterior proximal portion of the stem. The large flat has a small recess 24 formed as a female Morse taper for assembly of a humeral socket. The stem also has a small flat 26 machined on the anterior proximal portion of the stem. The small flat has a threaded insertion/extraction hole 28. These allow ease of fixturing for machining and give rotational stability when implanted. The small recess has an axis forming an angle of about 150 degrees to the central axis. The prior art primary stems are at 135 degrees. The added 15 degrees allows the stem to be more medial which allows for proper tension relationship with the deltoid and increases the range of motion. The lower portion of the stem has four axial cement grooves 30 distally for added fixation and rotational stability. The stem is designed to be seated approximately 12 millimeters below the humeral osteotomy. The proximal humeral bone is reamed so the humeral socket can be recessed to thereby provide for proper tension and bone support of the structural socket and the deltoid and increased range of motion.

Next provided is a humeral socket 32. The socket is fabricated of ultra high molecular weight polyethylene. A backing plate 34 fabricated of titanium is attached to the socket. The backing plate has an upper generally cylindrical extent 36. The backing plate also has a lower extent 38 formed with a projection as a male Morse taper. The projection is adapted to be received in the small recess of the stem. The socket has an upper surface machined as a 32 millimeter diameter hemisphere for the receipt of a glenoid head. This allows for 4 millimeters of wear by the polyethylene socket. The polyethylene captures about one-third of the glenoid head. The backing plate is formed with a linear recess 40 machined adjacent to the bottom of the socket after assembly. A locking pin 44 extends through a recess 46 in the socket to prevent the backing plate from backing out of the socket. A 2 millimeter lip 48 is formed around the bottom of the backing plate adjacent to the linear recess to provide lever-out stability with the socket. The sizes are neutral, about +4 millimeters and +8 millimeters.

A glenoid head 52 fabricated of cobalt chrome is next provided. The glenoid head is formed in a hemispherical configuration with a 32 millimeter diameter. The glenoid head is adapted to be received in the socket. A machined cylindrical pocket 54 and a glenoid baseplate are provided. The pocket allows the head to mate with the glenoid baseplate with no gap. The head has a large recess formed as a female Morse taper for assembly to a glenoid baseplate. The head has a small cylindrical neck 56 adjacent to the pocket to prevent contact of the socket in articulation. There is one head height.

Lastly, a baseplate 60 is fabricated of titanium. The baseplate is machined from titanium bar. The baseplate has a cylindrical central part having a diameter of 26 millimeters. Four mounting screw holes 62 are equally spaced and extend through the cylindrical central part and four 3.5 millimeter screws are provided for fixation. The holes and screws are off-axis to allow 12 degrees angulation of screws in any direction. A 6.5 millimeter by 2.5 millimeter long cancellous bone screw 64 is machined in the center of the exterior part of the baseplate which provides greater fixation. An enlarged interior projection 66 has a male Morse taper for assembly to the head. A 3.5 millimeter hexagonal recess 68 is formed in the end of the interior projection to assist during insertion. The baseplate also includes a titanium porous coating 70 for bone in-growth.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A reverse shoulder prosthesis system for providing a shoulder prosthesis with improved fabrication, installation and utilization capabilities comprising, in combination:

a humeral stem fabricated of titanium with a lower cylindrical portion having a diameter of between about 6 millimeters and 10 millimeters and an upper cylindrical portion having a diameter of between about 8 millimeters and 14 millimeters and an intermediate conical portion therebetween, the lower and upper and intermediate portions having a common central axis, the stem having a large flat machined on the posterior proximal portion of the stem with a small recess as a female Morse taper for assembly of a humeral socket and a small flat machined on the anterior proximal portion of the stem with a threaded insertion/extraction hole, the small recess having an axis forming an angle of about 150 degrees to the central axis, the lower portion of the stem having four axial cement grooves distally for added fixation and rotational stability;

a humeral socket fabricated of ultra high molecular weight polyethylene and an attached backing plate fabricated of titanium, the backing plate having an upper generally cylindrical extent and a lower extent formed with a projection as a male Morse taper received in the small recess of the stem, the socket having an upper surface machined as a 32 millimeter diameter hemisphere for the receipt of a glenoid head, the backing plate being formed with a linear recess machined adjacent to the bottom of the socket after assembly, a locking pin extending through a recess in the socket to prevent the backing plate from backing out of the socket, a 2 millimeter lip formed around the bottom of the backing plate adjacent to the linear recess to provide lever-out stability with the socket;

a glenoid head fabricated of cobalt chrome formed in a hemispherical configuration with a 32 millimeter diameter to be received in the socket with a cylindrical pocket machined therein to allow the head to mate with a glenoid baseplate with no gap, the head having a large recess as a female Morse taper for assembly to a glenoid baseplate, the head having a small cylindrical neck adjacent to the pocket to prevent contact of the socket in articulation; and a baseplate fabricated of titanium with an exterior part and a cylindrical central part having a diameter of 26 millimeters with mounting screw holes equally spaced and extending there through with four 3.5 millimeter screws for fixation, the holes and screws being off-axis to allow 12 degrees angulation of screws in any direction, a 6.5 millimeter by 2.5 millimeter long cancellous bone screw machined in the center of the exterior part the baseplate which provides greater fixation, and an enlarged interior projection as a male Morse taper for assembly to the head and a 3.5 millimeter hexagonal recess formed in the end of the interior projection to assist during insertion, the baseplate also including a titanium porous coating for bone in-growth.

2. A reverse shoulder prosthesis system comprising:

a humeral stem with a lower cylindrical portion and an upper cylindrical portion and an intermediate conical portion there between and a central axis, the stem having a large flat with a small recess, the small recess having an axis forming an angle of about 150 degrees to the central axis;

a humeral socket and an attached backing plate formed with a projection as a male Morse taper received in the small recess of the stem, the socket having an upper surface machined as a hemisphere;

a glenoid head formed in a hemispherical configuration with a cylindrical pocket; and a baseplate with a cylindrical central part and an exterior part, a long cancellous bone screw machined in the center of the exterior part of the baseplate, and an enlarged interior projection for assembly to the head.

3. The system as set forth in claim 2 wherein the humeral stem is fabricated of titanium.

4. The system as set forth in claim 2 wherein the humeral socket is fabricated of ultra high molecular weight polyethylene and further including the attached backing plate fabricated of titanium.

5. The system as set forth in claim 2 wherein the humeral socket is fabricated of ultra high molecular weight polyethylene.

6. The system as set forth in claim 2 wherein the glenoid head is fabricated of cobalt chrome.

7. The system as set forth in claim 2 wherein the baseplate is fabricated of titanium.

* * * * *

UNITED STATES PATENT AND TRADEMARK OFFICE
CERTIFICATE OF CORRECTION

PATENT NO.    : 6,790,234 B1
DATED         : September 14, 2004
INVENTOR(S)   : Mark A. Frankle and Dennis C. Moad It is certified that error appears in the above-identified patent and that said Letters Patent is hereby corrected as shown below:

<u>Title page,</u>
Item [76], Inventors, should read as follows:

-- [76]  Inventors:  Mark A. Frankle, 5124 Longfellow Ave., Tampa, FL (US) 33629 and Dennis C. Moad, 906 San Jacinto Street, Lochart, Texas (US) 78644 --

Signed and Sealed this

Twenty-third Day of November, 2004

JON W. DUDAS
*Director of the United States Patent and Trademark Office*